United States Patent
Arocha et al.

(10) Patent No.: US 12,053,341 B2
(45) Date of Patent: Aug. 6, 2024

(54) DEVICE, METHOD, AND SYSTEM FOR AUTOMATED DISPENSING OF PERIODONTAL MEDICATION

(71) Applicant: PharmaPhD, Inc., Plantation, FL (US)

(72) Inventors: Max Arocha, Plantation, FL (US); Murtaza Amir, Cumberland, MD (US); Adnan Qayyum, Bethlehem, PA (US)

(73) Assignee: PharmaPhD II, LLC, Plantation, FL (US)

( * ) Notice: Subject to any disclaimer, the term of this patent is extended or adjusted under 35 U.S.C. 154(b) by 144 days.

(21) Appl. No.: 17/194,157

(22) Filed: Mar. 5, 2021

(65) Prior Publication Data

US 2021/0338401 A1    Nov. 4, 2021

Related U.S. Application Data

(62) Division of application No. 16/028,395, filed on Jul. 5, 2018, now abandoned.

(60) Provisional application No. 62/528,563, filed on Jul. 5, 2017.

(51) Int. Cl.
| | |
|---|---|
| *A61C 19/06* | (2006.01) |
| *A61K 9/00* | (2006.01) |
| *A61M 5/32* | (2006.01) |
| *A61M 31/00* | (2006.01) |
| *A61M 37/00* | (2006.01) |
| *A61L 2/26* | (2006.01) |

(52) U.S. Cl.
CPC .......... *A61C 19/063* (2013.01); *A61K 9/0063* (2013.01); *A61M 5/3286* (2013.01); *A61M 31/007* (2013.01); *A61M 37/0069* (2013.01); *A61L 2/26* (2013.01); *A61L 2202/24* (2013.01); *A61M 2005/3206* (2013.01); *A61M 2210/0631* (2013.01)

(58) Field of Classification Search
CPC ...... A61M 3/00; A61M 3/0279; A61M 5/178; A61M 5/20; A61M 5/2033; A61M 5/3205; A61M 5/3286; A61M 5/34; A61M 2005/2026; A61M 2005/3206; A61M 31/007; A61M 37/0069; A61M 2205/195; A61M 2210/0631; A61C 19/063; A61K 9/0063
See application file for complete search history.

(56) References Cited

U.S. PATENT DOCUMENTS

| | | | | |
|---|---|---|---|---|
| 3,545,435 A | * | 12/1970 | Augenstein | A61C 17/38 601/162 |
| 4,474,308 A | * | 10/1984 | Bergeron | A61J 7/0053 221/24 |
| 4,841,985 A | * | 6/1989 | Wanamaker | A61B 5/15003 600/583 |
| 5,250,026 A | * | 10/1993 | Ehrlich | A61M 37/0069 604/117 |

(Continued)

*Primary Examiner* — Kami A Bosworth
(74) *Attorney, Agent, or Firm* — Ted Whitlock Registered Patent Attorney, PA (57) ABSTRACT

A device for the treatment of periodontal disease includes a handle that has a configuration familiar to dental professionals, and a detachable tip or cartridge, that is locked into the handle when use. The device provides for automatically delivering a single dose of medicament, such as a powdered preparation of antibiotic, to a periodontal pocket for treatment of infection or disease.

8 Claims, 11 Drawing Sheets

(56) References Cited

U.S. PATENT DOCUMENTS

| | | | | |
|---|---|---|---|---|
| 5,284,479 | A | * | 2/1994 | de Jong ............ A61M 37/0069 604/137 |
| 5,858,006 | A | * | 1/1999 | Van der AA ....... A61M 5/3286 604/239 |
| 6,682,348 | B2 | * | 1/2004 | Lawter .............. B05C 17/00593 604/218 |
| 6,702,790 | B1 | * | 3/2004 | Ross ................... A61M 5/3286 604/239 |
| 2004/0162524 | A1 | * | 8/2004 | Schiff ............... A61M 5/31595 604/209 |
| 2011/0313429 | A1 | * | 12/2011 | Anderson .......... A61B 17/3205 606/131 |
| 2013/0178822 | A1 | * | 7/2013 | Hickingbotham ...... A61M 5/00 604/152 |

\* cited by examiner

DEVICE, METHOD, AND SYSTEM FOR AUTOMATED DISPENSING OF PERIODONTAL MEDICATION

BACKGROUND

Periodontitis is a bacterial infection of the oral tissues that retain the teeth in the jawbone. Untreated, periodontitis can damage the ligaments and bone, and can cause formation of pockets between the teeth and periodontal tissue (gums) which can result in loosening or even loss of teeth held by the surrounding infected tissue.

Currently, preferred methods of treating periodontal disease involve delivering therapeutic agents, such as antibiotics, directly to and within these periodontal pockets. However, arriving at methods and delivery devices that provide successful administration of antibiotic or other therapeutic agents to the periodontal pocket has proven to be difficult.

The development of microparticles in dry form has improved the delivery of antibiotic agents to the periodontal pocket. Devices have also been developed for delivery and administration of these microparticles. For example, U.S. Pat. Nos. 5,236,355, 5,500,228, and 5,622,498 generally describe a syringe having a tip which contains the microparticulate therapeutic agent, wherein the tip is adapted for delivery of microparticles to the periodontal pocket, and a plunger which forces the therapeutic agent from the tip and into the periodontal pocket. However, these devices were disadvantageous for delivering an accurate and consistent dose of the antibiotic.

Later improvements to these devices are described in U.S. Pat. Nos. 6,682,348 and 7,699,609 having a removable tip comprising the plunger, wherein the tip is fitted onto a specially adapted syringe-like actuator. However, these actuators can be difficult to manipulate wherein proper use for administration is an acquired skill, even by experienced professionals.

Accordingly, what is needed in the art is a readily manipulated delivery system and apparatus for administering one or more consistent, accurate dose of a therapeutic agent, such as a dry microparticulate antibiotic to the periodontal pocket of a patient.

SUMMARY OF THE INVENTION

The instant invention concerns a device, method, or system for automated dispensing of periodontal medication directly to a periodontal pocket. The present invention comprises a periodontal medicament dispenser and cartridge and, more particularly a medicament dispenser for treating clinical disease of a periodontal pocket and a quick release cartridge in the form of a medicament delivery tip structured to hold and dispense a material comprising a medicament capable of treating clinical disease of the periodontal pocket.

The dispenser and tip work together as the operator slides the tip, preferably wedge-shaped or elliptical in its outer diameter, under the gum, and more particularly between the tooth and gum where periodontal infection or disease is present. The wedge design of the tip facilitates delivery of medication to the target site of the periodontal pocket.

The system provides a medicament delivery or dispensing device comprising an actuator body, serving as a handle (referred to herein as the "actuator handle portion", "actuator," "handle" or "handle portion"). The actuator body has an open end to engage a detachable delivery tip containing a plunger and a single dose of medicament. The actuator functions as a handle and houses a mechanism, preferably a spring-loaded shaft or push-rod that contacts and engages the plunger disposed within the tip. Release of stored energy in the mechanism, e.g., release of the spring-loaded shaft or push-rod, by the push of a button or other release of a "catch," thereby automatically and consistently causes delivery of an accurate dose of a medicament from the tip, and preferably directly into the periodontal pocket.

The actuator handle portion housing bounds an energy storage and release mechanism, e.g., a spring-loaded shaft or push-rod, which contacts a plunger provided within the delivery tip, thereby pushing the plunger a predetermined or "set" distance when the stored or spring-loaded energy is released, for accurate and consistent dispensing of the medicament from the lumen of the tip to the periodontal pocket. The actuator housing further comprises openings along its length to allow push-buttons, "catch" means, or locking means, or the like, to protrude from the inside to the outside of the housing. These protruding buttons or the like are used for setting and releasing the stored energy of the housed mechanism and can be advantageously and conveniently manipulated by the user during operation of the device, preferably with one hand.

The delivery tip comprises a generally elongate tube, having an internal lumen or bore disposed throughout its entire length (e.g. an opening that extends from one end to the other), preferably round and placed centrally within the tip. The outer diameter or circumference of the tip can be tapered, forming an elongate, generally cone-shaped tip, wherein one end (referred to herein as the "engagement end" of the tip) has an outer diameter sized to engage with the open end of the actuator and an inner diameter sized to receive the shaft or push-rod. The other, opposite end of the tip, from which medicament is delivered (herein referred to as the "delivery end" of the tip), has an outer diameter that is smaller or reduced in size compared to the engagement end, and is configured to fit within the periodontal pocket.

In a preferred embodiment, the outer aspect or profile of the delivery end of the tip has a tapered outer diameter thereby becoming elliptical in shape, the outer aspect being thereby flattened and consequently reduced in size to advantageously form a two-pronged wedge-shaped end for insertion between a tooth and surrounding gum creating what can be referred to as a "two-pronged bevel" or a "two-pronged beveled delivery port", thereby allowing the tip to be positioned within the periodontal pocket for delivery of the medicament.

In addition, the delivery segment or delivery end of the tip can be configured such that the end from which medicament is delivered is cut or formed at an acute angle, rather than at a right angle, in relation to the sides of the tip. The delivery end of the tip can alternatively include one or more cutouts or slots. These angled, cut-out- or slotted configurations of the tip delivery end can facilitate exposure of a portion of the medicament disposed in the tip, whereby the tissue contacts the exposed portion of the medicament when delivered and can facilitate secure placement of the medicament in the desired position.

In addition, the tip can be configured or formed wherein the delivery end segment is angled, preferably 90-degrees or less, and more preferably between 10-degrees to about 70-degrees, and most preferably between about 30-degrees and 50-degrees, away from the longitudinal axis of the tip. The angled configuration can be a curved angle to facilitate smooth movement of the plunger within the lumen. Providing an angled tip can be advantageous for inserting the tip into the periodontal pocket for delivery of the medicament.

In one preferred embodiment, the tip can be deformable, whereby the user can form the desired angle of the delivery segment of the tip.

In one embodiment of the invention, a plurality of detachable tips can be provided, packaged together, in a tray or other holding case, such that the engagement end of the tip can be fitted onto the open end of the actuator/handle portion without being touched by human hands. This can reduce the chance of contamination of the tip being engaged onto the actuator handle and can reduce the likelihood of cross-contamination of the other tips in the storage tray.

The apparatus disclosed herein includes a reusable actuator handle that is fitted with disposable cartridges or tips, loaded with a composition, for example, a precise dose of a therapeutic agent. This saves the clinician time, eliminates guessing as to the proper dose, and reduces the amount of disposable instrumentation, making the process more economical.

Preferably, the therapeutic agent loaded into the cartridge or tip in a predetermined quantity, e.g., a single dose, of dry microparticles, for example, an antibiotic such as or the like, and at least a portion of the dry particles are within the tip. A cap or closure member may be fitted over the tip to maintain the integrity of the composition until use is desired.

Thus, a device for the treatment of periodontal disease of the subject invention includes an ergonomic body that has a "pen-style" configuration, and a medicament loaded delivery tip or cartridge that is locked into the actuator body when use. The tip, preferably having an elliptical or ovoid opening at the delivery end, can penetrate into periodontal pockets space for direct application of the periodontal therapeutic powdered agent.

Exact dosage of dry periodontal therapeutic powdered is extremely important when efficient periodontal topical therapeutics are used to treat periodontal disease. In this invention, such exact dosing is provided by controlled or regulated movement of the shaft and plunger working together, e.g., controlling the distance the shaft and plunger move with each operation to achieve an automated delivery of the therapeutic.

Preferably, the apparatus of the present invention can dispense a 1 mg dose of a microparticle powder of an antibiotic, e.g., minocycline, per periodontal pocket. A preferred formulation for the powdered therapeutic agent comprises a controlled-release preparation, e.g., coated particles, matrix formulation or the like, as is well known in the art.

Another aspect of the subject invention is a pre-filled delivery tip or cartridge, comprising a single dose of a microparticulate therapeutic agent, such as antibiotic powder, e.g., minocycline microparticles. Each tip is configured to detachably affix to the open end of the handle portion of the apparatus with a single push. For example, in one embodiment the detachable tip is configured as a "snap-on" tip which locks into the actuator handle for and during use, and which is detachable by a release mechanism, e.g., button or switch provided on the body of the handle, which is controlled by the user. In yet another embodiment, the tip is configured with an outer flange at its engagement end that engages a catch disposed at the open engagement end of the actuator handle. A compression spring within the actuator housing is fashioned to compress when the tip is seated and locked into communication with the actuator. The catch retains the tip in position during use. Once the medicament is expelled, the delivery tip undergoes detachment from the actuator upon release of the catch via release of energy stored as compression force within the compressed spring. Preferably, the tip or cartridge is disposable. Additionally, the tip and handle portion are preferably both autoclavable or otherwise capable of being sterilized using heat, steam or chemical exposure.

One preferred embodiment of a tip according to the subject invention comprises an elliptical outer diameter (to form a wedge-shaped tip end for accessing the periodontal pocket) but a substantially circular (round) inner diameter which can reduce friction and the distance (stroke) of movement of the plunger that is required to dispense the medicament material from the tip, as compared to a tip end having an elliptical inner diameter.

Another embodiment of the subject invention is directed to a method for treating periodontal disease. This method involves providing an apparatus and tip as described herein. The handle portion of the tip can be provided with the tip already affixed to the handle portion or can be provided separately. If provided separately, e.g., in a tray holding a plurality of tips, the user can affix the tip to the handle portion by pushing the handle portion onto a selected tip until it locks into the handle portion. The handle portion with affixed tip can then be maneuvered to the target periodontal pocket for treatment, wherein the dose of the therapeutic agent is delivered by pushing a button on the handle portion, thereby releasing the energy stored by the spring-loaded shaft. This shaft engages and pushes the plunger within the tip a pre-determined distance to deliver the therapeutic agent to the target periodontal pocket.

The tip can then be released from the handle portion by a release mechanism and disposed into a biological hazard waste disposal container.

A further step according to the invention is to affix a subsequent tip onto the handle portion of the apparatus and repeat the procedure. This procedure can be repeated several times and is limited only by the number of periodontal pockets to be treated.

More particularly, the present invention is directed to a medicament delivery device having an actuator that includes a housing serving as a handle and having an open distal end in communication with a medicament delivery tip. The tip is detachably affixed to the actuator and has an axial bore longitudinally disposed therethrough with a single dose of medicament and a medicament plunger contained therein. The medicament is housed at the distal end of the delivery tip distal to the plunger. The actuator also includes an internally disposed push rod coupled to a compression spring that is capable of storing energy when compressed. The rod and compression spring are capable of being locked into spring loaded configuration by a catch mechanism upon compression of the spring. The release of stored energy in the compressed spring is actuated by a single-action release mechanism operatively coupled to said catch mechanism. The release results in the automated movement of the push rod for engagement with the medicament plunger to deliver the medicament.

Accordingly, herein is provided various embodiments, features and advantages of the present invention that will be apparent to those of ordinary skill in the art in view of the following detailed description of the invention and accompanying drawings.

BRIEF DESCRIPTION OF THE DRAWINGS

The objects and details of the invention can be understood by reference to the drawings accompanying this application, as summarized below.

DETAILED DESCRIPTION OF THE INVENTION

Figure 1A:
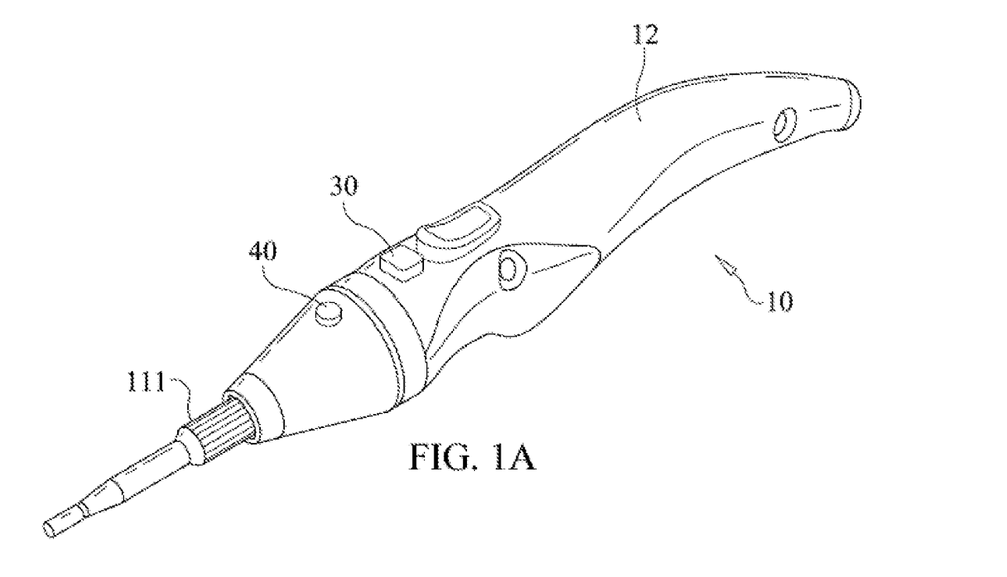
FIG. 1A is a perspective view of one embodiment of a device according to the subject invention having an actuator handle and a detachable delivery tip (shown capped).
Figure 1B:
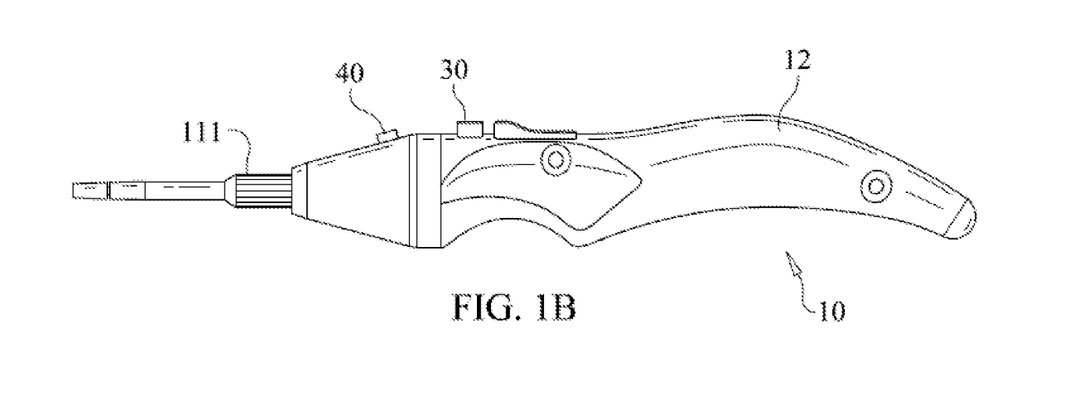
FIG. 1B is a lateral view of one embodiment of the present invention as shown in FIG. 1A.

Turning now to the FIGS. 1-12, the system and device, and components thereof, comprises a medicament delivery device 10 comprising an actuator portion or body 12 as shown in FIGS. 1A and 1B, serving as a handle (referred to herein as the "actuator handle portion", "actuator," "handle" or "handle portion"), and a detachable delivery tip 111.

Figure 2:
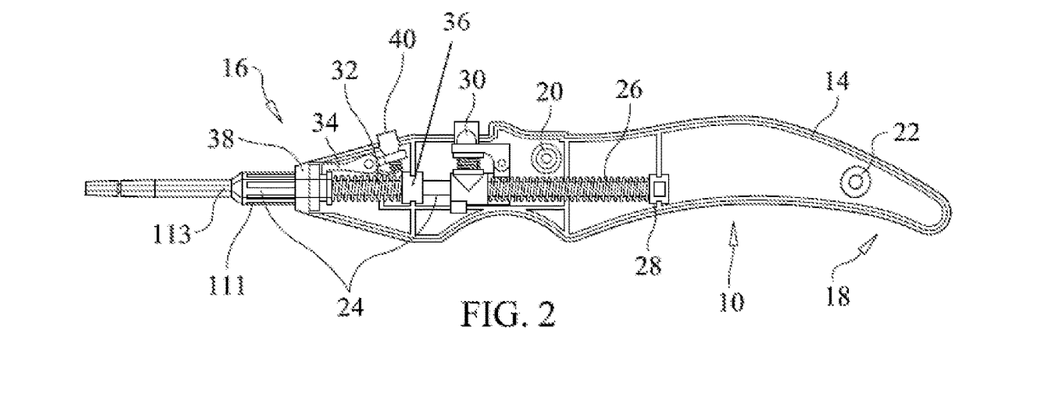
FIG. 2 is a cross-sectional view of FIG. 1B illustrating the actuator mechanism disposed within the actuator handle portion.

Preferably, the actuator handle portion 12 is ergonomically configured and weight-balanced for comfort in the hand and easy manipulation by the user. In a preferred embodiment, the actuator handle portion of the device comprises housing 14 which is generally elongate in shape, having two ends, one end of which is open, and configured to receive and detachably engage a delivery tip as can be seen in FIG. 2 taken with FIG. 3.

Figure 3:
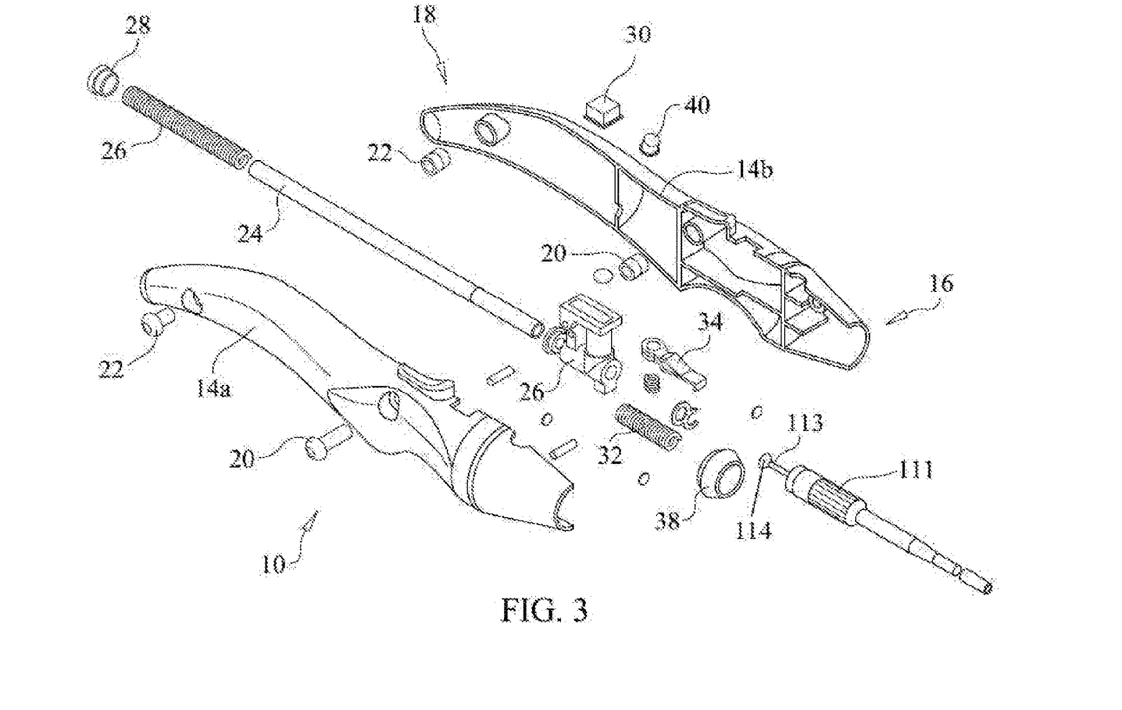
FIG. 3 is an exploded perspective view of one embodiment of a device according to the subject invention having an actuator handle and a detachable delivery tip with a cap.

Turning briefly to FIG. 3, the open end of actuator handle 12 is shown at engagement end 16 or distal end 16, the other end being shown as proximal end 18. It will be appreciated by those of ordinary skill in the medical and dental arts that depending upon the context, the terms "proximal" and "distal" as used herein shall indicate either directional movement or the position of device components relative to one another as observed from the perspective of the device operator; proximal being closer to the operator and distal being further from the operator. For purposes of further clarification, distal end 16 of dispensing device 10 shall be the end away from the operator and closest to the patient and when the device is held by the operator; the proximal end being opposite thereto, namely closest to the operator and away from the patient. Furthermore, a part or component X is said to be "distal from or to" part or component Y when the relative position of part X is more remote or away from the operator than Y if he or she were using the device in a clinical procedure.

Housing 14 may be formed by any number of acceptable and readily available techniques well known to the medical and dental device design and fabrication arts. Suitable medical grade materials for manufacturing medical and dental are commonly fabricated from polymeric materials. Such polymers may include but are not limited to thermo-setting polymers, thermoplastic polymers, and mixtures thereof. Moreover, it will be further apparent to those skilled in the art that selection of such polymers or copolymers should be such that the resulting polymeric matrix is of sufficient durability and rigidity.

For example, a suitable housing may be formed from standard blow molded polymers as an integral body or in separate attachable halves such as 14a and 14b as shown in FIG. 3, whereby the two halves can be secured to one another by any suitable attachment means such as, for example, machine screws employed with a nut or other suitable securing member to receive the screw for adjoining the halves once the internal components housed within the actuator handle are in place (see, for example, housing attachments 20 and 22).

Turning again to FIG. 3, housing 14 bounds an energy storage and release mechanism for delivering a force that automatically imparts movement to push rod 24 once released. One preferred embodiment for such a mechanism is a spring-loaded shaft such as a push-rod coupled to a compression spring. As used herein, the term "spring loaded" describes a moveable member (e.g. the push rod) capable of movement imparted to it by the release of energy stored in a compressed spring that is coupled to the member thereby acting on the member to reposition it from a first position to a second position by virtue of the coupling.

In such an arrangement, typical "loading" of stored energy into the compression spring occurs by an initial movement of the member by the application of manual or other outside force that subjects the member to the compressive forces building and captured in the spring as it undergoes deformation by virtue of its coupling to the member being moved. The spring undergoes deformation pursuant to the member being moved from a first position wherein the spring is substantially non-deformed and relaxed to a second position wherein the spring is deformed into a compressed state whereupon it embodies stored or potential energy due to compression in accordance with Hooke's Law. Consequently, the member is now subject to the compressive force of the spring by virtue of the coupling and can be said to be "spring loaded".

Such spring-loaded configurations have been well-known to the mechanical arts for centuries and there is no shortage of designs that can be readily incorporated for use in the present invention with minimal adaptation. It will be further appreciated that once compressed, the spring must be maintained, either directly or indirectly, in the compressed configuration by some suitable retention means.

Turning again to FIGS. 2 and 3 for an exemplification of the foregoing, push rod 24 is positioned within the housing 14 along its longitudinal axis and is aligned by way of and slideably received through support 26 for contact with plunger head 114 of medicament plunger 113 contained in delivery tip 111 when it is detachably affixed to distal end 16 of actuator handle 12. Compression spring 26 is positioned such that push rod 24 is passed through the spring helices and is coupled to spring 26 so that movement of the push rod in the proximal direction "loads" compression forces onto the spring as it compresses against spring stop 28. Once loaded, any number of retention mechanisms well known in the art such as a pawls or catches may be employed to maintain spring 26 and rod 24 in a "spring loaded" configuration.

In turn, these retention mechanisms can be operatively coupled to a release mechanism that releases the spring and rod from the spring-loaded configuration, whereupon the stored energy of the spring automatically moves the rod distally to extend a determined distance into the internal aspect of the tip and to engage the medicament plunger disposed therein. A plethora of suitable retention and release mechanisms are readily available and well known in mechanical arts and the ordinary artisan is more than capable of adapting any number of such mechanisms for incorporation into the present invention, providing that the dimensions and configurations of the same are compatible with placement within the housing such that the operator's access to any triggers or buttons maintains the ergonomic advantages of the device as contemplated herein. Examples of these advantages include ease in manipulation and handling, as well as maneuverability, similar to a writing implement; and the capability of operation by a forefinger or other digit and are not operated by pushing a plunger with a thumb, as in a syringe design.

Shy of the foregoing, the artisan's selection of a suitable design for a retention member and release mechanism is only limited by his or her imagination. However, it is preferable that the release mechanism is a single-action type such that the operator need only push a button, pull a trigger, etc. to achieve what may be referred to a as a "one-click" actuation to release the dispensing force housed in the spring-loaded push rod. This "one-click" actuation design is advantageous to the clinician as it provides for an automated, reproducible delivery of medication to the periodontal tissues wherein the force required to deliver the medication is provided by the mechanical, release of spring-loaded energy of the apparatus and is not dependent on the physical hand strength of the user. This advantage becomes even more significant for the periodontist who may undergo hand strength exhaustion due to multiple procedures performed on various patients over the course of an entire work day.

Figure 4:
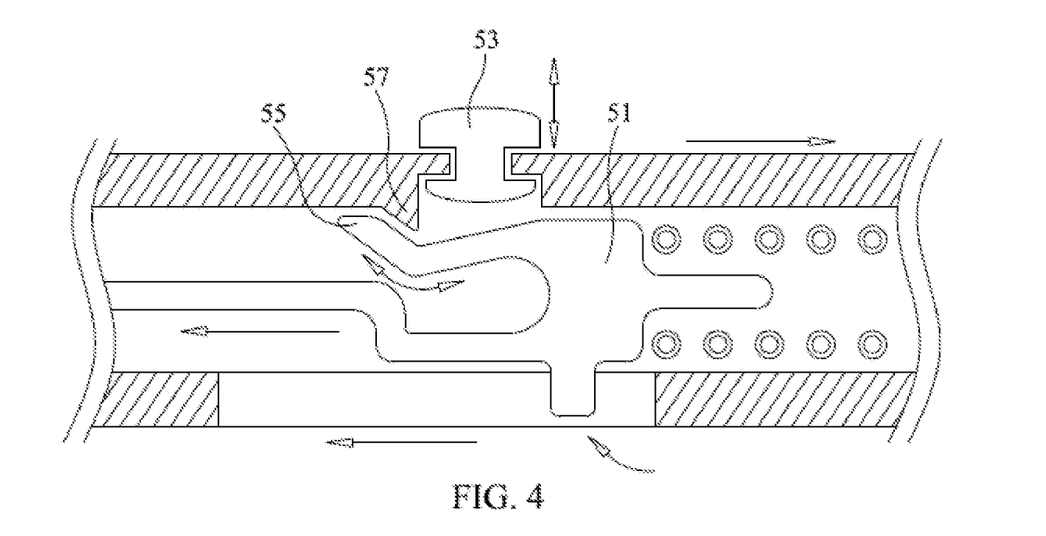
FIG. 4 is a lateral cross-sectional view of one embodiment of a combination catch and "single click" release mechanism for operative engagement with the spring-loaded push rod of the present invention.
Figure 5:
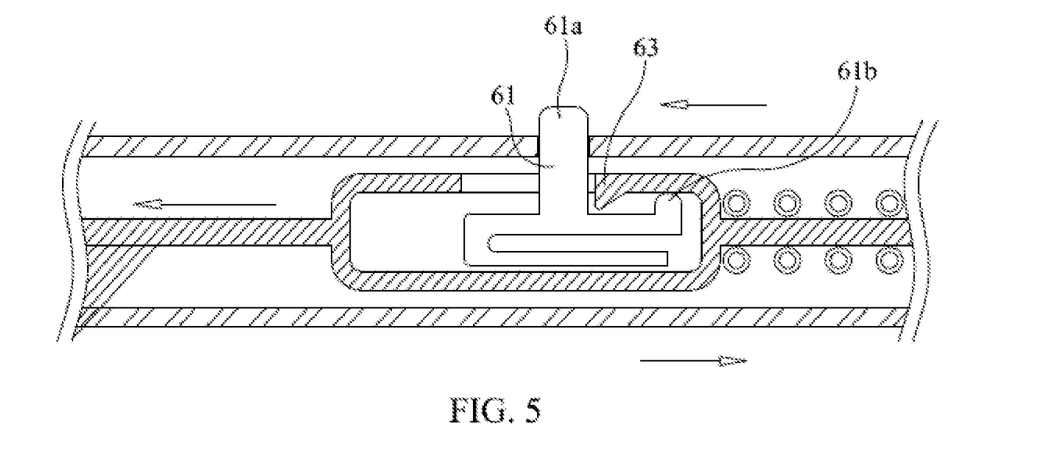
FIG. 5 is a lateral cross-sectional view of an alternative embodiment of a combination catch and "single click" release mechanism for operative engagement with the spring-loaded push rod of the present invention.

By way of example only, FIGS. 4 and 5 illustrate various embodiments for a combination retention and release mechanism that may be adapted for use with the present invention. Turning to FIG. 4, a combination retention and release mechanism is disclosed wherein retention member 51 resides adjacent to operator button 53 whereupon depression of button 53 operates to contact and depress catch member 55 such that it clears stop 57 to release the spring-loaded rod when incorporated into the present invention. An alternative embodiment is shown in FIG. 5 wherein retention member 61 includes operator button 61a integrally formed with catch member 61b such that depressing button 61a operates to depress catch member 61b by virtue of the integral design thereby clearing stop 63.

Turning once again to FIGS. 2 and 3, it will be readily appreciated by the artisan that the actuator button for releasing the spring-loaded push rod should preferably reside somewhere along the distal half of the top external aspect of housing 14 as illustrated by actuator button 30 as shown in FIGS. 1-3. It will also be appreciated that the retention and release mechanism may be fabricated in conjunction with support 26 so as to afford optimal internal positioning.

Figure 6:
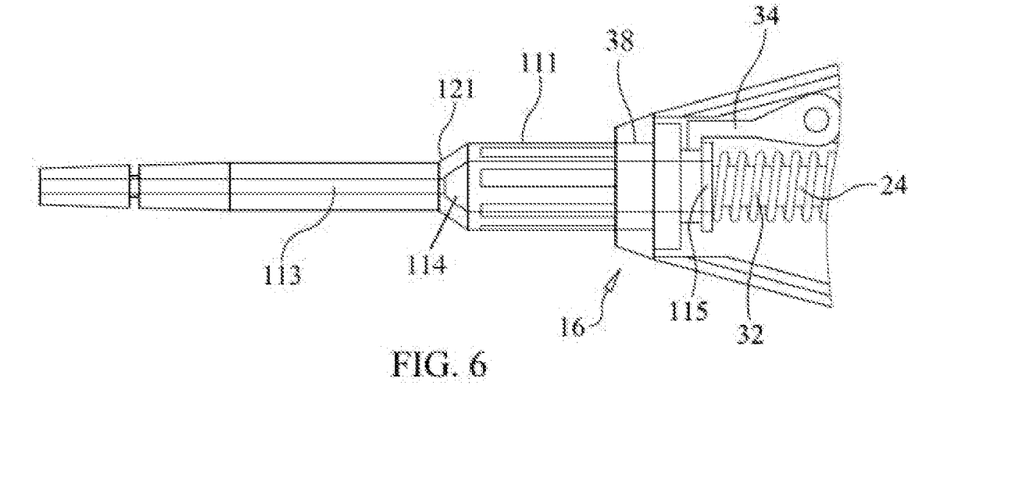
FIG. 6 is an enlarged lateral view of the engagement end of the actuator handle for the device embodiment shown in FIG. 2 illustrating a straight-tip embodiment for the delivery tip.

In addition to the spring-loaded push rod of the present invention, actuator handle 12 further comprises a coupling mechanism at the distal end of housing 14 for detachably affixing delivery tip 111 to the actuator. Turning to FIG. 2 taken together with FIGS. 3 and 6, the coupling mechanism preferably utilizes compression spring 32 in conjunction with coupling latch 34 to secure tip 111 to the housing 14 by way of tip flange 115 which provides coupling latch 34 with a lip by which to secure the tip to the actuator, details of which are best seen in FIG. 6.

In order to properly seat and affix the delivery tip to the actuator handle, the operator must initially spring load push rod 24 by manually pushing it toward the proximal end of housing 14 until it locks into place by virtue of the retention mechanism. It will be appreciated that actuator 12 may be designed to further comprise a loading armature or the like to facilitate movement of push rod 24 and compression spring 26 to the spring-loaded position.

Once the push rod has been spring loaded, the distal or engagement end 16 of the actuator is ready to receive a delivery tip. While the delivery tip may be manually attached to the actuator by hand, it is preferable to have the delivery tip in a suitable instrument tray that allows the operator to advance the engagement end of the actuator handle toward the receiving or proximal end of the tip for attachment without manually handling the tip. As the actuator is advanced toward the tip, flange 115 enters the engagement end 16 of actuator 12 and compresses compression spring 32 against spring stop 36 until flange 115 is trapped by latch 34. Importantly, push rod 24 is free to pass slideably through the helices of compression spring 32 during both spring loading of the rod and its release for contact with the medicament plunger.

Proper alignment and seating of the delivery tip relative to the actuator is preferably facilitated by bushing 38 that allows the delivery tip to seat firmly against the actuator placing medicament plunger 113 in alignment to receive engagement from push rod 24 via plunger head 114. Coupling latch 34 is operatively coupled to a delivery tip release trigger or button 40 which is positioned on the external aspect of the housing so as to be readily accessible to the operator's forefinger when holding the actuator in one hand. Preferably, coupling latch 34 is fabricated in a hinged configuration such that depressing release button 40 raises the latch out of communication with tip flange 115 allowing the compression spring 32 to decompress expelling the tip away from the actuator handle for sanitary disposal.

Figure 8:
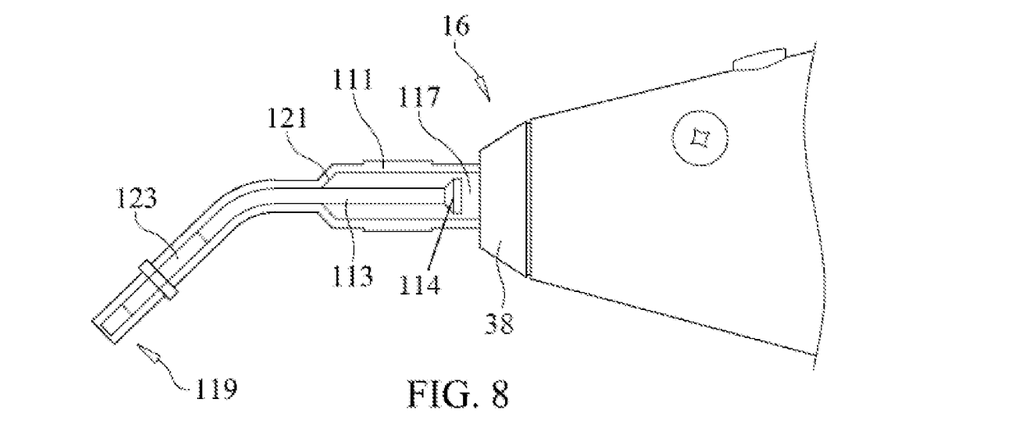
FIG. 8 is a partial lateral view of the engagement end of the actuator handle of the present invention shown with a cross sectional lateral view of an angled delivery tip illustrating a medicament plunger and medicament bolus disposed therein.

Turning first to FIG. 8 taken together with FIG. 6, it will be appreciated that delivery tip 111 includes internal bore 117 that is substantially round and centered within the tip. The bore runs longitudinally through the entire length of the tip from its proximal end which engages the actuator to its distal end that terminates in medicament exit port 119. It will be appreciated that internal bore 117 includes a tapered stepdown in diameter positioned within the tip to function as plunger stop 121 which impedes the plunger from any further distal movement. As will be further noted from FIGS. 3, 6 and 8, taken together, push rod 24 contacts plunger 113 at the proximal end of the plunger via plunger head 114, thereby driving the distal end of the plunger toward the medicament exit port 119 to expel medicament bolus 123 from tip 111 until the distal movement of plunger head 114 is halted by plunger stop 121. Accordingly, when the delivery tip is properly seated and affixed to the actuator handle, the movement of the plunger is limited to a predetermined stroke distance that is a function of the delivery tip shape and size when contacted by the push rod. It will be appreciated by those of ordinary skill in the medical and dental device fabrication arts that the stroke distance of the plunger can be varied by altering the delivery tip design. This design confines the plunger's movement to a predetermined or "set" distance for accurate and consistent dispensing of the medicament out of exit port 119 and into the periodontal pocket.

Figure 7A:
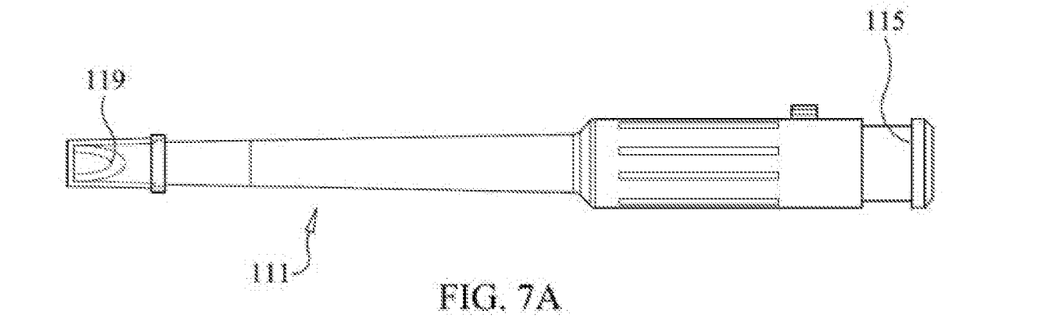
FIG. 7A is a lateral view of a straight-tip embodiment for the delivery tip of the present invention having an elliptical cut-out of the tip end (a.k.a. the "two-pronged bevel"), shown capped.
Figure 7B:
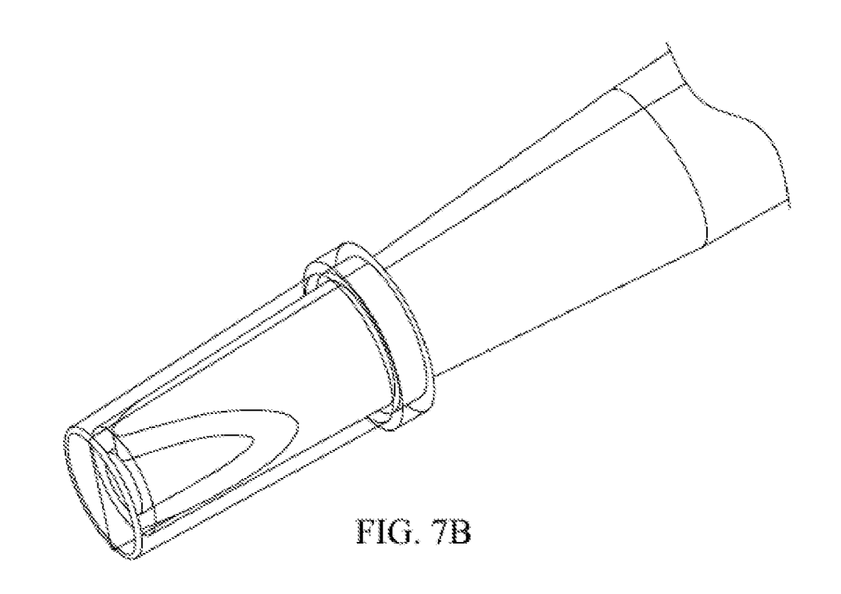
FIG. 7B an enlarged perspective view of the tip embodiment shown in FIG. 7A.
Figure 7C:
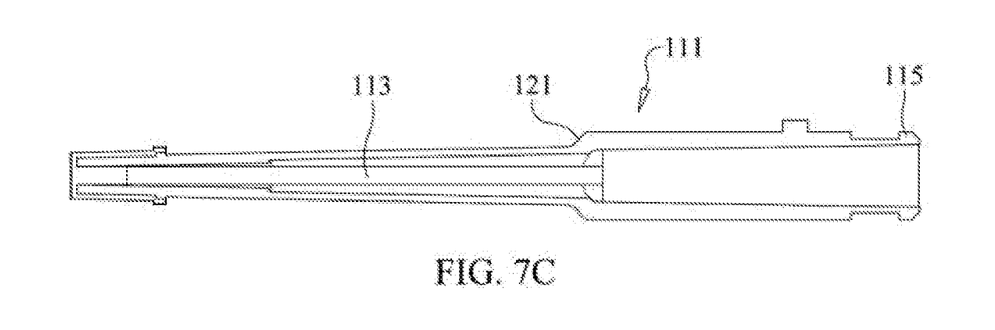
FIG. 7C is a lateral cross-sectional view of the tip embodiment shown in FIG. 7A.
Figure 7D:
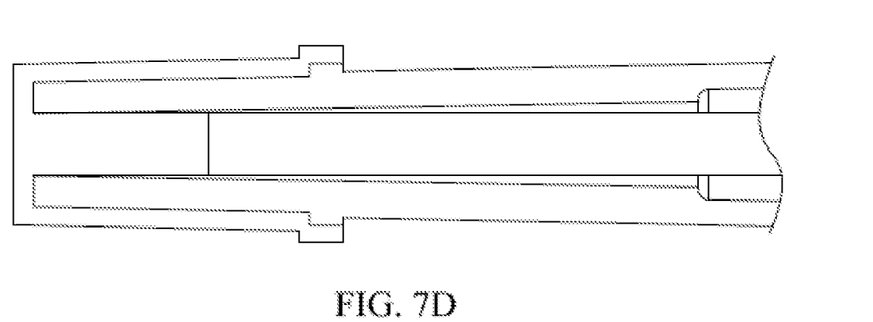
FIG. 7D is an enlarged view of the medicament delivery end of the tip shown in FIG. 7C.
Figure 11A:
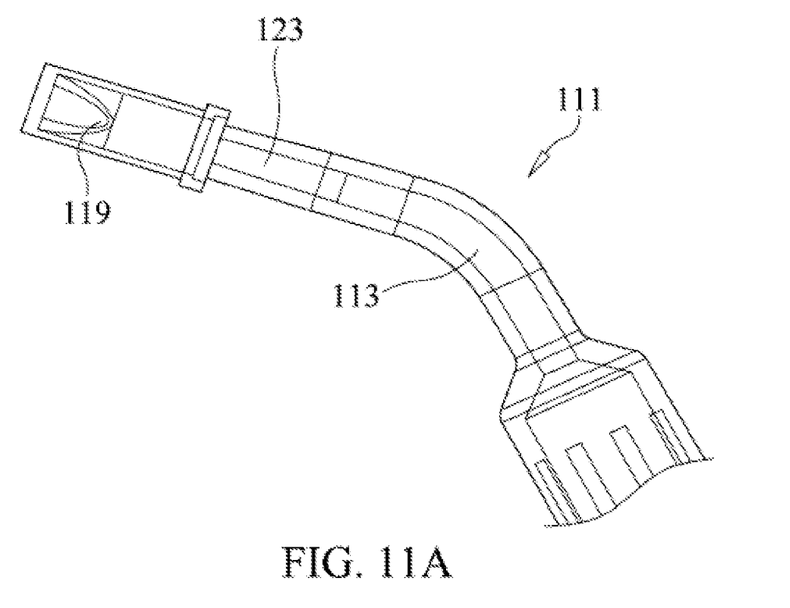
FIG. 11A is a partial lateral view of angled tip embodiment for a detachable tip according to the subject invention and illustrating a pre-placed medicament dose housed within the delivery end of the tip prior to expulsion by the plunger (partially shown) with a semi-translucent cap engaged on the end of the delivery tip.
Figure 11B:
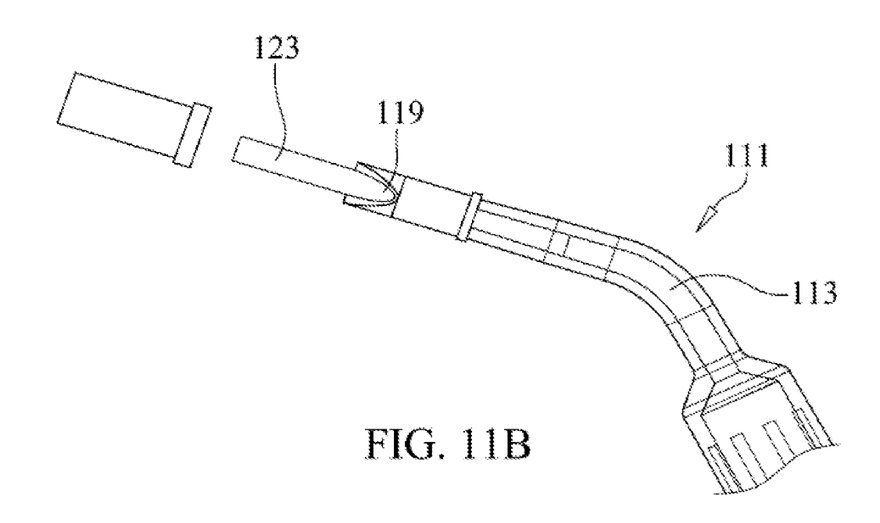
FIG. 11B is a lateral view of an angled tip configuration for a detachable tip according to the subject invention, illustrating a cap removed from the end of the tip.

Turning to FIGS. 7A and 7C as well as FIGS. 11A and 11B, it will be appreciated that the outer diameter of the delivery tip can be tapered, forming an elongate, generally cone-shaped tip, wherein the proximal end (also referred to herein as the "engagement end" of the tip) has an outer diameter sized to engage with the distal engagement end of the actuator handle portion, and an inner diameter sized to receive push-rod 24 which is capable of extending a predetermined distance into the internal aspect of the delivery tip to engage medicament plunger 113 and drive it distally until the plunger head is stopped by plunger stop 121, the particulars of which can be best seen in FIG. 6. The other, opposite end of the tip terminates in medicament exit port 119 from which medicament bolus 123 is delivered to the gingival sulcus (herein referred to as the "delivery end" of the tip) and has an outer diameter that is smaller or reduced in size compared to the engagement end and is configured to fit within the periodontal pocket.

Figure 10:
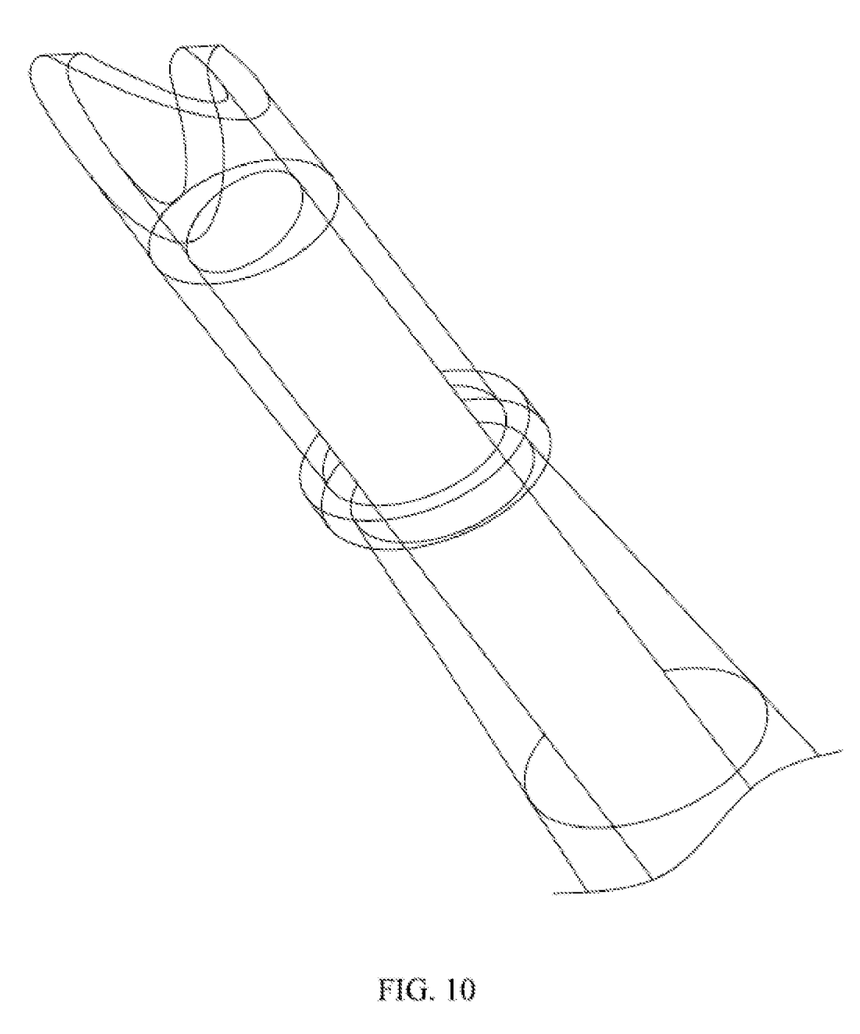
FIG. 10 shows an enlarged perspective view of a tip end configured to have a slotted or cut-out opening at the tip end.

A preferred embodiment of the tip portion of the has a "stepped" or "stepped down" tapering from the proximal to the distal end of the tip best seen in FIGS. 7A and 7C taken together with FIG. 10. Accordingly, the tip is sequentially tapered in a step-wise fashion whereby the outer circumference of the tip is progressively reduced forming contiguous engagement and delivery segments of the tip distinguishable from one another by their outer diameters. The tip portion may include one or more "middle segments" having intermediate-sized diameters compared with the engagement and delivery segments, formed between the engagement and delivery segments. These middle or intermediate segments can provide extended length to the tip and can provide support along the length of the tip, resisting undesired bending or breaking of the tip.

In a stepped tapering configuration, the engagement end forms a first or engagement segment of the tip and is sized to engage with the open end of the actuator handle portion as can be best seen in FIG. 7C. This first segment preferably has an outer diameter which is substantially circular in cross-section. The inner diameter of the engagement end of the tip is sized to receive the shaft or push-rod extending from the actuator handle portion. The engagement end segment is formed contiguous with delivery segment. The outer diameter of the delivery segment of the tip can be tapered along its axial length, having reduced size at the delivery end of the tip. The lumen or bore within the delivery segment is preferably the same throughout the entirety of its length and forms an opening at the delivery end of the tip such that the medicament can exit from the tip and be delivered to the periodontal pocket.

Figure 12A:
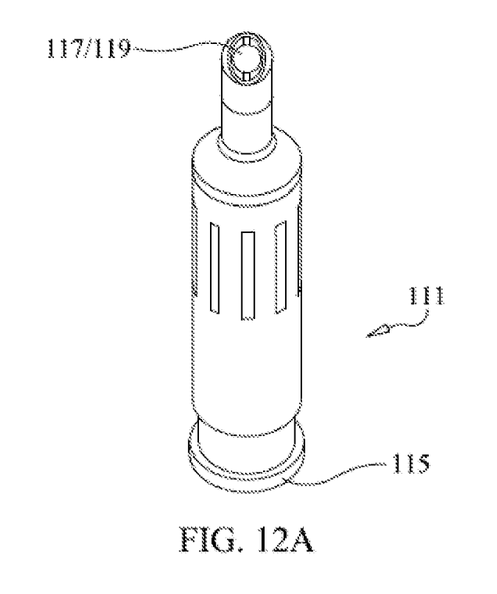
FIG. 12A is an elevational front view of an angled tip embodiment for a detachable tip according to the subject invention, illustrating an elliptical cut-out or slotted embodiment of the tip end and round cross-section of the inner diameter of the tip end.
Figure 12B:
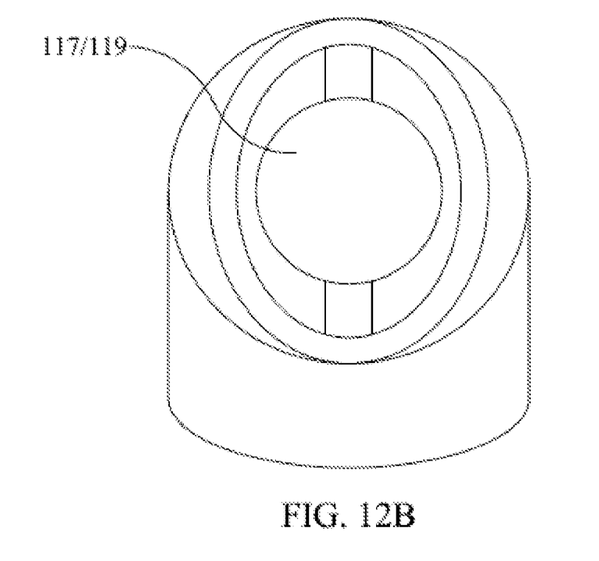
FIG. 12B is an enlarged detail view of the tip embodiment shown in 12A.

In a preferred embodiment, the outer circumference of the most distal end of the delivery tip undergoes a change from a substantial round shape to a more elliptical shape as can be seen in FIGS. 12A and 12B. This circumferential change is the outer aspect of the delivery tube still allows for the internal bore to maintain its substantially round integrity as can best be seen in FIG. 12B. Accordingly, the outer aspect of the delivery tip becomes effectively flattened and thereby facilitates entry of the distal end of the tip into the gingival sulcus.

Figure 9A:
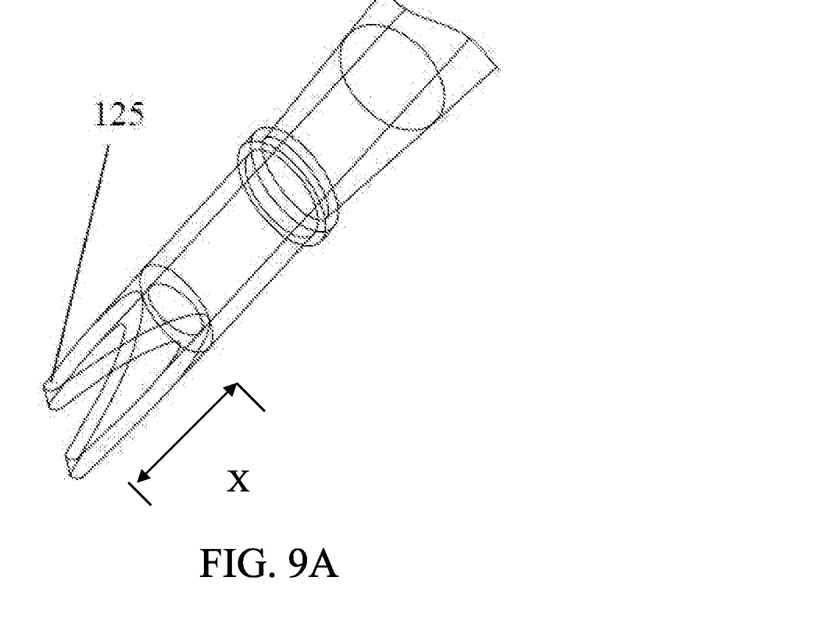
FIG. 9A shows a perspective view of one embodiment of a delivery tip of the present invention having a medicament exit port configured with an angular cut of length X to allow for increased gingival exposure to and retention of the medicament during delivery.
Figure 9B:
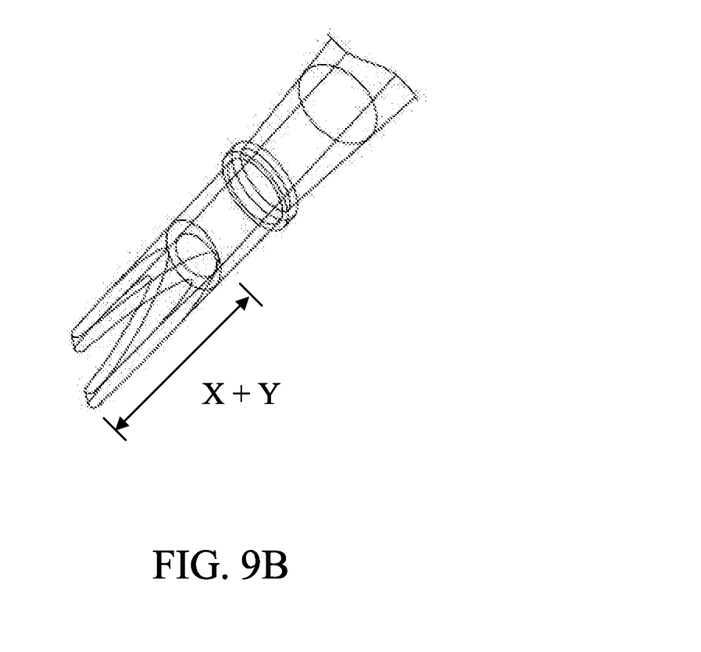
FIG. 9B shows a perspective view of one embodiment of a delivery tip of the present invention having a medicament exit port configured with an angular cut of length X+Y to allow for greater increased gingival exposure to and retention of the medicament during delivery by lengthening the angular cut.
Figure 9C:
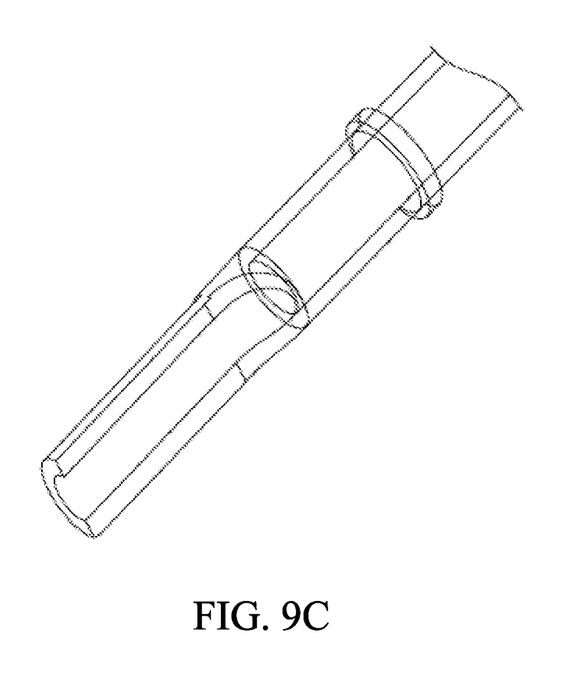
FIG. 9C shows a perspective view of a varied embodiment of a delivery tip medicament exit ports shown in FIGS. 9A and 9B configured with a different cut-away to allow for greater increased gingival exposure to and retention of the medicament during delivery.

In addition, the distal end of the delivery tip can be configured such that the medicament exit port is fashioned or cut at an acute angle to achieve a wedge-like appearance. For example, FIG. 9A shows a perspective view of one embodiment of a delivery tip of the present invention having a medicament exit port configured with an angular cut of length X to allow for increased gingival exposure to and retention of the medicament during delivery. Such angular cuts may be of varied lengths whereby, generally, the longer the cut, the greater the gingival exposure to and retention of the medicament in the desired area of treatment (e.g. the periodontal pocket). FIG. 9C shows a perspective view of a varied embodiment of a delivery tip medicament exit ports shown in FIGS. 9A and 9B configured with a different cut-away to similarly allow for greater increased gingival exposure to and retention of the medicament during delivery.

Turning to again to FIGS. 9A and 9B, it can be appreciated how the angular cuts advantageously form a two-pronged wedge-shaped end 125 for insertion between a tooth and surrounding gum thereby facilitating placement of the distal most end of the tip within the periodontal pocket for delivery of the medicament.

In yet another embodiment, the delivery tip can be configured or formed wherein the delivery end segment is angled, preferably 90-degrees or less which is exemplified in FIG. 8 taken together with FIGS. 11A and 11B. The angled configuration is preferably formed as a curved angle to facilitate smooth movement of medicament plunger 113 within the internal bore 117. Providing an angled tip can be advantageous for inserting the tip into the periodontal pocket for delivery of the medicament. In one preferred embodiment, the tip can be deformable, whereby the user can form the desired angle of the delivery segment of the tip.

In one embodiment of the invention, a plurality of detachable tips can be provided, packaged together, in a tray or other holding case, such that the engagement end of the tip can be fitted onto the open end of the actuator handle portion without being touched by human hands. This can reduce the chance of contamination of the tip being engaged onto the actuator handle and can reduce the likelihood of cross-contamination of the other tips in the storage tray.

The apparatus disclosed herein includes a reusable actuator handle that is fitted with disposable tips, loaded with a composition, for example, a precise dose of a therapeutic agent. This saves the clinician time, eliminates guessing as to the proper dose, and reduces the amount of disposable instrumentation, making the process more economical.

Preferably, the therapeutic agent loaded into the tip in a predetermined quantity, (e.g., a single dose of dry microparticles, for example) comprising an antibiotic or other therapeutic, wherein at least a portion of the dry particles are within the tip and predominantly range in size from about 10 to about 250 µm. Preferably, the cap or closure member may be fitted over the tip to maintain the integrity of the composition until use is desired.

The present invention improves upon prior devices in, at least the following:
a. the apparatus has an ergonomic design, fashioned for manipulation and handling, as well as maneuverability, similar to a writing implement;
b. the apparatus does not have a syringe design, thus, also facilitating manipulation and handling by a user, and further being better suited for patient afraid of syringes.
c. These design features provide the capability of operation by a forefinger or other digit and are not operated by pushing a plunger with a thumb, as in a syringe design.
d. Provides a "push-button" or "one-click" delivery of medication to a periodontal pocket wherein the force required to deliver the medication is provided by the mechanical, release of spring-loaded energy of the apparatus and is not dependent on the physical hand strength of the user.

Exact dosage of dry periodontal therapeutic powdered is extremely important when efficient periodontal topical therapeutics are used to treat periodontal disease. In this invention, such exact dosing is provided by controlled or regulated movement of the shaft and plunger working together, e.g., controlling the distance the shaft and plunger move with each operation. It will be further appreciated by those of ordinary skill in the medical and dental arts that dispensing a medicament to a desired tissue treatment area under an automated force such as compressed air or pressurized liquids for example, must be cautiously performed to avoid injuring the surrounding tissues while maintaining adequate force to maximize the delivery of the medicament to the desired treatment area.

For example, it is generally accepted by the dental clinician that attached gingival tissue may tolerate up to about 200 psi for up to several seconds without inducing irreversible tissue damage, the upper limit of which should never exceed 300 psi. Compromised tissue is clearly more vulnerable. Accordingly, it has been discovered that the device of the present invention may be designed to safely deliver medicament to the gingiva using a force up to about 100 psi on undamaged tissue while about 50 to 90 or higher psi is recommended for inflamed or ulcerated tissue. As such, the design and manufacture of the actuator handle must integrate adequate testing and calibration of the force to be delivered to the medicament plunger bearing in mind that the delivery tip dimensions and configuration will likewise have an effect on such force.

Preferably, the apparatus of the present invention can dispense a 1 mg dose of a microparticle powder of an antibiotic, e.g., minocycline, per periodontal pocket. A preferred formulation for the powdered therapeutic agent comprises a controlled-release preparation, e.g., coated particles, matrix formulation or the like, as is well known in the art.

Another aspect of the subject invention is a pre-filled tip or cartridge, comprising a single dose of a microparticulate therapeutic agent, such as antibiotic powder, e g, minocycline microparticles. Each tip is configured to detachably affix to the open end of the handle portion of the apparatus with a single push. In other words, the detachable tip is configured as a "snap-on" tip which locks into the handle for and during use, and which is detachable by a release mechanism, e.g., button or switch provided on the body of the handle, which is controlled by the user. Preferably, the tip or cartridge is disposable. Preferably, the tip and handle portion are both autoclavable or otherwise capable of being sterilized using heat, steam or chemical exposure.

Advantages of the wedge-shaped end of the hollow tip include:
a. easy dispensing (low force required) to deliver the dry powder into a relatively narrow periodontal pocket.
b. facilitates access to the periodontal pocket by penetrating the pocket by sliding the tip against the tooth for gum-tooth separation (acting as a periodontal pocket expander)
c. facilitates powder delivery within constricted pocket. The hollow wedge design of the tip increases the surface area of the tip exit Advantages of the detachable or "snap-on" tip mechanism include:
a. Provides a hand-free tip release
b. Provides audible conformation upon engagement
c. Automated tip release
d. Provides multiple (5) secure position along the axis The features provided in the subject apparatus advantageously overcome the anatomical/clinical limitations of currently marketed devices having a round-ended tip design.

The elliptical slot tip design (wedge effect) provides an advantage for sliding/guiding the tip into the gum pocket, but further significantly facilitates in forcing/delivering the powder medication into the narrow space of the periodontal pocket. This design of the tip end addresses the problem of not to increasing the tip diameter due to the anatomy/space available in the periodontal pocket. So, to make this happen we would have to increase length of the stroke.

A preferred embodiment of a tip according to the subject invention comprises an elliptical outer diameter (to form a wedge-shaped tip for accessing the periodontal pocket) but a circular (round) inner diameter which can reduce the distance (stroke) of movement of the plunger that is required to dispense the medicament material from the tip, as compared to a tip end having an elliptical inner diameter. A substantially circular bore (inner diameter) of the tip can also be advantageous for facilitating the movement of a plunger having a substantially circular (circular or round in cross-section) outer diameter.

An elliptical tip end reduces the cross-sectional area and therefore increases the length of the (stroke distance)

required of the plunger to dispense and deliver the medicament from the tip. A sample calculation is as follows:

Example 1

If the stroke distance is the same (7 mm in length).
Round inner diameter of the tip:
(1.04 m Ø) Drug Chamber: {[π×(0.104 cm)2]÷4}×0.7 cm=0.0059 cc
Elliptical inner diameter of the tip:
(0.7 mm×0.3 mm) drug chamber: (0.07/2 cm×0.03/2 cm)×π×0.7 cm=0.0011 cc
Therefore, maintain the same volume (0.0059 cc) the length/stroke becomes 5 times longer for a tip having an elliptical inner diameter as compared to a round or circular inner diameter.

Another embodiment of the subject invention is directed to a method for treating periodontal disease. This method involves providing an apparatus and tip as described herein. The handle portion of the tip can be provided with the tip already affixed to the handle portion or can be provided separately. If provided separately, e.g., in a tray holding a plurality of tips, the user can affix the tip to the handle portion by pushing the handle portion onto a selected tip until it locks into the handle portion. The handle portion with affixed tip can then be maneuvered to the target periodontal pocket for treatment, wherein the dose of the therapeutic agent is delivered by pushing a button on the handle portion, thereby releasing the energy stored by the spring-loaded shaft. This shaft engages and pushes the plunger within the tip a pre-determined distance to deliver the therapeutic agent to the target periodontal pocket.

The tip can then be released from the handle portion by a release mechanism and disposed into a biological hazard waste disposal container.

A further step according to the invention is to affix a subsequent tip onto the handle portion of the apparatus and repeat the procedure. This procedure can be repeated several times and is limited only by the number of periodontal pockets to be treated.

While preferred embodiments of an apparatus, components and methods, have been described above, the description of the apparatus, components and methods above is exemplary only. Those skilled in the art will recognize or be able to ascertain using no more than routine experimentation, many equivalents to the specific embodiments of the invention described herein. Such equivalents are intended to be encompassed by the following claims.

What is claimed is:

1. A periodontal medicament delivery device comprising:
an actuator comprising a housing serving as a handle and having an open distal end in communication with
a medicament delivery tip detachably affixed to the actuator, said medicament delivery tip having an elliptical outer circumference, while maintaining a circular axial bore longitudinally disposed through the medicament delivery tip, the circular axial bore of the medicament delivery tip containing a single dose of medicament and a medicament plunger, said medicament being contained at a distal end of said medicament delivery tip, and distal to said medicament plunger, wherein the distal end of the medicament delivery tip comprises a first angular cut and a second angular cut, the first angular cut and the second angular cut being diametrically opposed relative to the circular axial bore, said first and second angular cuts providing a two-pronged beveled wedge configuration at said distal end of the medicament delivery tip, and wherein each prong of said two-pronged beveled wedge configuration has a rounded distal end;
wherein the actuator further comprises an internally disposed push rod coupled to a compression spring capable of storing energy when compressed, said push rod and said compression spring being lockable into a spring-loaded configuration by a catch upon compression of the compression spring;
wherein release of the stored energy in the compressed compression spring is actuated by a single-action release operatively coupled to said catch, wherein actuation of the release is configured to be operated by a forefinger or other digit and not operated by pushing a plunger with a thumb, wherein said actuation results in automated movement of the push rod to engage the medicament plunger to deliver the medicament.

2. The periodontal medicament delivery device of claim 1 wherein the release is actuated by a single-action operator button.

3. The periodontal medicament delivery device of claim 1 wherein the medicament comprises dry microparticulates.

4. The periodontal medicament delivery device of claim 3 wherein the microparticulates comprise particles having sizes from about 10 µm to 250 µm.

5. The periodontal medicament delivery device of claim 1 wherein the medicament comprises an antibiotic.

6. The periodontal medicament delivery device of claim 5 wherein the antibiotic is minocycline.

7. The periodontal medicament delivery device of claim 1 wherein the automated movement of the push rod occurs with a force of about 50 psi to about 300 psi.

8. The periodontal medicament delivery device of claim 1 further comprising:
a coupling for detachably affixing the medicament delivery tip to the actuator, said coupling comprising a second compression spring in communication with a proximal end of the medicament delivery tip and being lockable into a spring-loaded configuration by a second catch upon compression of the second compression spring when the medicament delivery tip is affixed to the actuator and wherein release of the second catch is actuated by a single-action operator button operatively coupled to said second catch to detach and release the medicament delivery tip from the actuator.

* * * * *